United States Patent [19]

Thoemel et al.

[11] 4,399,297
[45] Aug. 16, 1983

[54] POLYALKOXYCARBINOL CINNAMATES AND PROTECTIVE SUN AGENTS CONTAINING THESE COMPOUNDS

[75] Inventors: Frank Thoemel; Karl Seib, both of Weinheim; Kurt Schneider, Bad Duerkheim; Paul Naegele, Neuhofen, all of Fed. Rep. of Germany

[73] Assignee: BASF Aktiengesellschaft, Rheinland-Pfalz, Fed. Rep. of Germany

[21] Appl. No.: 279,795

[22] Filed: Jul. 2, 1981

[30] Foreign Application Priority Data

Jul. 26, 1980 [DE] Fed. Rep. of Germany ....... 3028503

[51] Int. Cl.³ .............................................. C07C 69/76
[52] U.S. Cl. ..................................... 560/55; 424/307
[58] Field of Search ........................... 560/55; 424/307

[56] References Cited

U.S. PATENT DOCUMENTS

| 3,002,992 | 10/1961 | Wood | 560/55 |
| 3,817,876 | 6/1974 | Fukutani et al. | 560/55 |
| 3,937,810 | 2/1976 | Mathur et al. | 560/55 |
| 4,322,544 | 3/1982 | Okazaki et al. | 560/55 |

FOREIGN PATENT DOCUMENTS

| 1543387 | 6/1972 | Fed. Rep. of Germany | 560/55 |
| 2529511 | 1/1977 | Fed. Rep. of Germany | 560/55 |
| 2036033 | 6/1980 | United Kingdom | 560/55 |

OTHER PUBLICATIONS

Chemical Abstracts, vol. 74, No. 24, Jun. 14, 1971.
P. Eiden et al., "Analysis of Sun Protective Agents", p. 319, Abstract No. 130283h.
Deut. Apoth. Ztg., vol. 111, No. 4, 1971, pp. 118 to 120.
Von R. Voegeli, "Ueber die Auswahl von Modernen Sonnenschutzmitteln," *Chemische Rundschau*, vol. 24, No. 43, pp. 1097-1098 (1971).

*Primary Examiner*—Paul J. Killos
*Attorney, Agent, or Firm*—Oblon, Fisher, Spivak, McClelland & Maier

[57] ABSTRACT

Compounds of the formula I

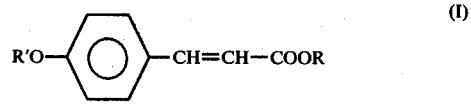

where R is a polyethylene glycol radical of 3 to 60 chain members or a polypropylene glycol radical of 3 to 60 chain members or the radical of an ethylene oxide/propylene oxide block polymer of average molecular weight from 300 to 8,500, and R' is straight-chain or branched alkyl of 1 to 10 carbon atoms, or benzyl.

2 Claims, No Drawings

POLYALKOXYCARBINOL CINNAMATES AND PROTECTIVE SUN AGENTS CONTAINING THESE COMPOUNDS

The present invention relates to novel cinnamic acid esters which are etherified at the phenolic hydroxyl group and polyoxyalkylated at the carboxylic acid group, to their preparation, to agents containing these compounds and to their use as protective sun agents for the human skin, and as light stabilizers and ultraviolet stabilizers in the industrial sector.

It is known that the region of from 280 to 350 nm of sunlight or artificial light sources is responsible for the development of erythema of human skin, this light region being referred to as ultraviolet-B radiation. The maximum activity of ultraviolet radiation in respect of erythema formation is at 297 nm if the radiation intensity is equally great for all wavelengths. In sunlight, containing radiation of different intensity, the maximum effect is shifted to 308 nm. By using suitable filter substances for the ultraviolet-B range, erythema formation can be prevented or at least retarded. On the other hand, it is desired that pigment formation in the skin, ie. bronzing, should not be suppressed.

Ultraviolet radiation is furthermore an important factor in the aging of polymers and can also, for example, change the color of certain dyes, so that for these products, again, filter substances which act as stabilizers are virtually indispensable.

In the past 40 years, a large number of chemical compounds have been examined for filter action in the ultraviolet-B range. However, whether a substance which absorbs in the ultraviolet range is also a useful protective sun filter for human skin is critically affected by a number of other factors:

In addition to high filtering efficiency in the erythema-generating range, the substance should have a high transmission of the energy responsible for bronzing, should be very well tolerated by the skin and mucous membranes, and must be non-toxic. It must also be insensitive to oxidation and must not suffer any modification or discoloration as a result of exposure to ultraviolet. An appropriate formulation of the substance must have a good shelf like, be free from any intrinsic odor and be compatible with the carriers or diluents conventionally used.

The known ultraviolet filters often have the disadvantage that on storage they prove unstable to ultraviolet radiation or visible radiation and/or to air, and that they are converted to colored decomposition products, soil laundry or even prove harmful to the skin. Since protective sun agents are extensively used by persons who work out-of-doors and pursue sports such as swimming and diving, the agents must not be excessively easily removable from the skin by water or by perspiration.

In practice, only a relatively small number of substances which more or less conform to the stated requirements have found acceptance, as is shown, for example, in Chemische Rundschau 24, (1971), 1097 et seq. They include the p-methoxycinnamic acid esters which in physical, toxicological and dermatological respects are considered to be safe protective sun agents. Further, for example, German Pat. No. 1,543,387 discloses that polyoxyalkylated p-aminobenzoic acid esters can be used as protective sun agents. The polyoxyalkylation is effected by reacting the corresponding carboxylic acids or esters with alkylene oxides in the presence of alkali. The adduct formation with the alkylene oxides can take place both at the carboxylic acid group and at the amino group.

We have found that compounds of the general formula I

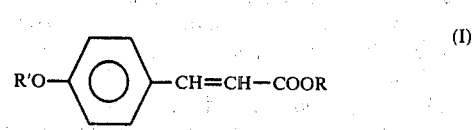
(I)

where R is a polyethylene glycol radical of 3 to 60 chain members or a polypropylene glycol radical of 3 to 60 chain members or the radical of a block polymer of ethylene oxide and propylene oxide, having an average molecular weight of from 300 to 8,500, and R' is straight-chain or branched alkyl of 1 to 10 carbon atoms, or benzyl, are excellent protective sun agents.

Amongst the polyethylene glycol and polypropylene glycol radicals R, those of 5 to 25 chain members are particularly preferred. The ethylene oxide/propylene oxide block polymers used are as a rule of the type of the general formula II

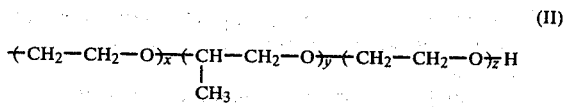
(II)

where x, y and z are each 1, 2 or 3, and consist of 10-80 percent by weight of ethylene oxide units and from 90 to 20 percent by weight of propylene oxide units.

Preferably, R' is alkyl of 1 to 4 carbon atoms.

The compounds of the formula I are prepared by reacting an alkyl p-hydroxycinnamate, which is appropriately etherified at the phenolic hydroxyl group, and where aklyl is of 1 to 5 carbon atoms, with a polyalkoxycarbinol HOR, where R has the meanings given for formula I, at from 50° to 250° C., in the presence of an alkali.

This reaction is carried out in a conventional manner. Preferably, the corresponding methyl cinnamates are used for the reaction. The catalyst used for the trans-esterification reaction is advantageously an alkali metal hydroxide, or an alcoholate or oxide of an element of main groups 1 and 2 of the periodic table, especially of sodium or potassium. The reaction is carried out with equimolar amounts of the reactants or with a slight excess of polyalkoxycarbinol, and in the presence of from 0.02 to 1 mole equivalent, preferably from 0.05 to 0.5 mole equivalent, of alkali, preferably at from 100° to 200° C., and under atmospheric pressure or, advantageously, under reduced pressure at from 0.1 to 200 mbar.

The reaction time is in general from 15 minutes to 20 hours. The course of the trans-esterification reaction can be followed by thin layer chromatography (silica gel prepared plates from Merck, 3:1 cyclohexane/ethyl acetate or methanol as the mobile phase, potassium permanganate in conc. sulfuric acid as the spray developer).

Advantageously, the catalyst, in aqueous or alcoholic solution, is added to the polyalkoxycarbinol at from 50° to 75° C. and water is removed from the mixture by distillation under reduced pressure. The cinnamic acid ester is then added and the mixture is heated, with or without reduction of pressure. At the end of the reaction, when the mixture has cooled to 50°–20° C., the alkali can be neutralized by adding dilute mineral acid, whilst stirring. The water which after neutralization is present in the reaction mixture is again removed by distillation under reduced pressure.

It is of interest that direct oxyalkylation of the etherified p-hydroxycinnamic acids is only moderately successful or even fails, and furthermore colored products can form.

The compounds according to the invention absorb, with very high extinction, in the ultraviolet-B range. By varying the ether and ester component, compounds having a particular consistency and the desired solubility properties can be prepared. The compounds to be used according to the invention are chemically easily accessible and constitute an advantageous enrichment of the range of available protective sun agents. A particular advantage of the compounds according to the invention is that they can have relatively good solubility in water. The compounds can exhibit high sun protection factors (cf. Ärztliche Kosmetologie, 7 (1977), 56 et seq.). The filter action in the ultraviolet-B range which aqueous solutions of the compounds exhibit can be utilized broadly for stabilizing cosmetic preparations, plastics, dyes, solvents and paints.

The compounds to be used according to the invention can also be employed in combination with other protective sun agents.

Accordingly, the present invention also relates to a protective sun agent, in the form of a cosmetic agent or formulation, which contains from 0.1 to 15 percent by weight, preferably from 2 to 8 percent by weight, of a compound of the formula I in addition to conventional solid, semi-solid or liquid carriers or diluents, or mixtures of these, with or without conventional cosmetic auxiliaries.

The nature of the carrier or diluent determines whether the finished protective sun agent is, for example, a solution, an oil, a cream, an ointment, a lotion, an emulsion or a powder. Formulations of this type may be found, for example, in Fette und Seifen 53 (1951), 694–699, Seifen, Öle, Fette, Wachse (1955), 147, and H. Janistyn, Handbuch der Kosmetika und Riechstoffe, volume 3 (1973).

Examples of conventional cosmetic auxiliaries which may be used as additives are emulsifiers, eg. fatty alcohol oxyethylates, sorbitan fatty acid esters or lanolin derivatives, thickeners, eg. carboxymethylcellulose and crosslinked polyacrylic acid, preservatives and perfumes.

Examples of suitable bases for protective sun oils are vegetable oils, eg. groundnut oil, olive oil, sesame oil, cottonseed oil, coconut oil, grapeseed oil and castor oil, as well as mineral oils, such as paraffin oil and especially liquid paraffin, synthetic fatty acid esters and the glycerides.

Examples of bases for ointments are white petroleum jelly, lanolin, emulsifying aqueous wool fat alcohols (eg. ®Eucerin) and polyethylene glycols.

Examples of bases for creams are glycerol, polysaccharides and tylose, or amongst fats and waxes, cetyl alcohol, lanolin, cacao butter, beeswax, stearic acid, stearyl alcohol, glycerol monostearate and natural and mineral oils and fats.

Examples of bases for emulsions are mixtures of stearyl glycol, a vegetable and/or mineral oil, such as almond oil, paraffin oil or white petroleum jelly, and water, or mixtures of ethyl alcohol, water, lanolin and tragacanth, or mixtures of ethyl alcohol, stearin and water, or tragacanth, glycerol, alcohol and water, or mixtures of stearic acid, paraffin oil, propyl or isopropyl alcohol and water.

The Examples which follow illustrate the invention without implying any limitation thereof.

EXAMPLE 1

1 g (25 millimoles) of sodium hydroxide dissolved in 3 ml of water is added to 150 g (136 millimoles) of polyethylene oxide of mean molecular weight 1,100. The mixture is stirred thoroughly for one minute at 75° C. and the pressure is reduced to 30 mbar. After 5 minutes, 24 g (125 millimoles) of methyl p-methoxycinnamate are added and the mixture is stirred for 4.5 hours at 150° C./30 mbar. To neutralize the basic catalyst, 10 ml of 10 percent strength sulfuric acid are then added, the mixture is stirred thoroughly for one minute at 50° C., and water is distilled off at 50° C./30 mbar. 158 g of water-soluble reaction product are obtained. Solidification point: 45°–55° C.; ultraviolet spectrum (in ethanol): $\lambda_{max}$ 308.8 nm, $\epsilon = 2.11 \times 10^4$, $E_{1\ cm}^{1\%}$ 3,165.

EXAMPLE 2

0.3 g (7.5 millimoles) of sodium hydroxide dissolved in 5 ml of water is added to 37.5 g (34 millimoles) of polyethylene oxide of mean molecular weight 1,100 at 75° C., the mixture is stirred for one minute and the pressure is reduced to 30 mbar. After 5 minutes, 9 g (31 millimoles) of methyl p-octoxycinnamate are added and the mixture is stirred for one hour at 150° C./30 mbar. It is then allowed to cool to 60° C., 5 ml of water and 1 ml of 10 percent strength sulfuric acid are added, and water is distilled off under 30 mbar whilst stirring the mixture and heating it for 10 minutes at 60° C. and then briefly to 150° C. 43 g of reaction product are obtained. Solidification point: 45°–55° C.; $\lambda_{max}$ (in ethanol) 309 nm, $\epsilon = 1.96 \times 10^4$, $E_{1\ cm}^{1\%} = 144$.

EXAMPLE 3

0.5 g of sodium hydroxide is added to 75 g (68 millimoles) of polyethylene oxide of mean molecular weight 1,100 at 150° C., and after 2 minutes 14.7 g (63 millimoles) of methyl p-tert.-butoxycinnamate are added. The mixture is heated for one hour at 150° C./30 mbar, the reaction product is allowed to cool to 50° C., and 6 ml of water and 5 ml of 10 percent strength sulfuric acid are added. After stirring for 5 minutes under atmospheric pressure, the pressure is reduced to 30 mbar and the mixture is heated to 150° C. in the course of 20 minutes. 83 g of reaction product are obtained. Solidification point: 40°–50° C.; $\lambda_{max}$ (in ethanol) 292.6 nm, $\epsilon = 1.88 \times 10^4$, $E_{1\ cm}^{1\%} = 144$.

EXAMPLE 4

0.35 g (8.8 millimoles) of sodium hydroxide, dissolved in 5 ml of water, is added, at room temperature, to 150 g (42.3 millimoles) of a block polymer of ethylene oxide and propylene oxide, of mean molecular weight 3,750, and the mixture is stirred for a few minutes and then heated for 5 minutes at 75° C./30 mbar. 7.3 g (38.1 millimoles) of methyl p-methoxycinnamate are then added and the mixture is heated for 3 hours at 150° C./30 mbar; 141 g of a fluid reaction product are obtained. $\lambda_{max}$ (in ethanol) 308.5 nm, $\epsilon = 1.9 \times 10^4$, $E_{1\ cm}^{1\%} = 51$.

EXAMPLE 5

1.0 g (15 millimoles) of sodium hydroxide, dissolved in 5 ml of water, is added to 75 g (125 millimoles) of polypropylene oxide, of mean molecular weight 600, at 75° C., the mixture is stirred for one minute and water is distilled off in the course of 5 minutes at 30 mbar. 21.7 g (113 millimoles) of methyl p-methoxycinnamate are then added and the mixture is heated at 200° C. for 6 hours under atmospheric pressure. It is allowed to cool to 50° C. and is neutralized, similarly to Example 1, with 3.5 ml of 10 percent strength sulfuric acid. 81 g of a fluid reaction product are obtained. $\lambda_{max}$ (in ethanol) 308.5 nm, $\epsilon = 1.66 \times 10^4$, $E_1\ _{cm}^{1\%} = 214$.

EXAMPLE 6

To prepare a protective sun milk, 1.7 g of an adduct of a fatty alcohol with 6 moles of ethylene oxide, 1.7 g of an adduct of a fatty alcohol with 25 moles of ethylene oxide, 4.3 go of decyl ethylhexanoate, 3.9 g of stearic acid triglyceride, 11.2 g of mineral oil, 3.5 g of stearic acid, 0.4 g of cetyl alcohol, 0.2 g of methyl p-hydroxybenzoate and 5.5 g of 2-ethylhexyl p-methoxycinnamate are melted together at 70° C. A mixture, also heated to 70° C., of 1.7 g of triethanolamine, 14.4 g of the product obtained according to Example 1, 0.3 g of perfume oil and 51.2 g of water is stirred into the preceding mixture, and stirring is continued until the batch reaches room temperature.

We claim:

1. A compound of the formula I:

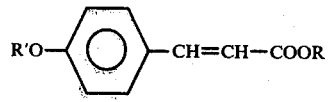

wherein R is a polyethylene glycol radical or a polypropylene glycol radical, each of said radicals having 5 to 25 chain members, and R' is a straight chain or branched alkyl of 1 to 4 carbon atoms.

2. A sun screen agent for the human skin, containing from 0.1 to 15% by weight of the compound of claim 1, together with conventional cosmetic carriers or diluents, optionally in the presence of conventional cosmetic auxiliaries.

* * * * *